United States Patent [19]

Wildfeuer

[11] Patent Number: 5,221,739
[45] Date of Patent: Jun. 22, 1993

[54] ACETYLATION OF 3-HYDROXYMETHYL CEPHALOSPORINS

[75] Inventor: Marvin E. Wildfeuer, Lafayette, Ind.

[73] Assignee: Eli Lilly and Company, Indianapolis, Ind.

[21] Appl. No.: 819,152

[22] Filed: Jan. 9, 1992

[51] Int. Cl.$^5$ .......................................... C07D 501/04
[52] U.S. Cl. ................................... 540/230; 540/215; 540/221; 540/222; 540/228
[58] Field of Search ............... 540/228, 230, 222, 221, 540/215

[56] References Cited

U.S. PATENT DOCUMENTS 3,445,463  5/1969  Heyningen .......................... 260/243
3,532,694  10/1970  Somerfield et al. ................. 260/243

FOREIGN PATENT DOCUMENTS 52-027792  3/1977  Japan.

OTHER PUBLICATIONS

Wallingford, et al., Alkyl Carbonates in Synthetic Chemistry, 63 *J. Chem. Soc.* 2252 (1941).

Abramavitch, et al., A New Method for the Preparation of Ethyl Propionylacetate and Certain Related β-keto esters, 64 *J. Chem. Soc.* 2271 (1942).

Heyningen, The Chemistry of Cephalosporin Antibiotics, 8 *J. Med. Chem.*, 22 (1965).

Huber, et al., Formation of Desacetylcephalosporin C in Cephalosporin C Fermentation, 16, *Applied Microbiology*, 1011 (1968).

Heyningen, Cephalosporins, 4 *Advanced Drug Research*, 27-29 (1968).

Tsushima, et al., A New Route to Semisynthetic Cephalosporins from Deacetylcephalosporin C., 27, *Chem. Pharm. Bull.* 696 (1979).

*Primary Examiner*—Nicholas S. Rizzo
*Attorney, Agent, or Firm*—James J. Sales; Leroy Whitaker

[57] ABSTRACT

Provided is a process for 3' acetylation of 3-hydroxymethylcephalosporins under aqueous conditions.

28 Claims, No Drawings

ACETYLATION OF 3-HYDROXYMETHYL CEPHALOSPORINS

FIELD OF THE INVENTION

The invention relates to a process for the preparation of beta lactam antibiotic intermediates, and more particularly to a process for the acetylation of 3-hydroxymethyl cephalosporins.

BACKGROUND OF THE INVENTION

The antibacterial compound cephalosporin C was first isolated by Newton and Abraham (*Nature*, 175:548, 1955). The antibacterial activity of cephalosporin C was generally low, however was still worthy of attention because it proved to be effective against organisms that had developed resistance to penicillins. Cephalosporin C is secreted by cephalosporium acremonium and is commercially produced in a fermentation broth containing cephalosporium acremonium cultures in an aqueous environment.

Cephalosporin C can be synthesized to 7-ACA, an important intermediate in the production of cephalosporin antibiotics such as cephaloridine, cefazolin, cefamandole, cefatrizine and cefazaflur. Conversion of Cephalosporin C to 7-ACA may be carried out by a chemical cleavage process, most generally using organic halides and $PCl_5$ (Huber, F. M., et al., *Cephalosporins and Penicillins*, (Academic Press, New York, pp 27-73, (1972)).

It has been reported that glutaryl 7-ACA may be formed by oxidative deamination of the $\alpha$-aminoadipoyl side chain of cephalosporin C, either chemically (Matsuda, et al., U.S. Pat. No. 3,960,662) or enzymatically (Fildes, et al., British Patent No. 1,272,769 (1972)). Thereafter, the glutaryl 7-ACA may be converted to 7-ACA by an enzymatic side chain cleavage (Suzuki, et al., U.S. Pat. No. 4,079,180).

The production and isolation of cephalosporin C has been complicated by the presence of desacetyl cephalosporin C in the fermentation broth. In the above described oxidation/7-position side chain cleavage process to obtain 7-ACA from cephalosporin C via glutaryl 7-ACA, it has been determined that not only glutaryl 7-ACA is formed after the first step, but so is desacetyl glutaryl 7-ACA. Up to this time it has been a practice to remove the desacetyl glutaryl 7-ACA. The two step process could afford additional benefits if a substantial amount of desacetyl glutaryl 7-ACA could be utilized.

At the present, acetylation of the 3-hydroxymethyl has not been able to be carried out on unprotected cephalosporins in aqueous solutions. Previous work by Van Heyningen (*J. Med. Chem.* 8, 22 (1965)) indicated that the 3' acetylation of desacetyl cephalosporins in aqueous media was hindered because of the ease with which the 3-hydroxymethyl lactonized with the 4 carboxyl to form the lactone.

It has been indicated that aromatic acid chlorides may be successfully used to esterify the 3'-hydroxyl of desacetyl cephalosporins. Summerfield, et al., U.S. Pat. No. 3,532,694 were able to acetylate the 3-hydroxymethyl group by first forming an ester at the 4-carboxy position to prevent lactone formation. This reaction was performed in anhydrous solvents using an organic base.

Tsushima, et al. (Japanese laid opened patent application No. 52027792; and *Chem. Pharm. Bull.* 27, 696 (1979)) were able to acetylate desacetyl cephalosporins in nonaqueous solvents such as dimethyl formamide.

It would be advantageous to provide a process for acetylation of 3-hydroxymethyl cephalosporin under aqueous conditions. The present invention is directed to such a process.

DESCRIPTION OF THE INVENTION

Provided is a process for the preparation of a compound of the formula

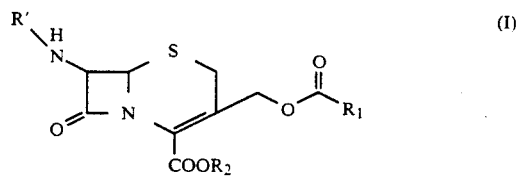

wherein
$R_1$ is the organic residue of an acid anhydride;
$R_2$ is hydrogen or a carboxy-protecting group; and
$R'$ is hydrogen, an amino-protecting group, or an acyl group of the formula

where R is the residue of a carboxylic acid; which comprises reacting a compound of the formula

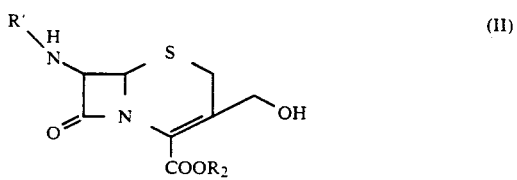

with an acid anhydride in the presence of a base in an aqueous solution.

The ability to carry out this reaction in water enables the acetylation to be accomplished at an early stage in purification from the broth. Particularly, the process allows the utilization of desacetyl glutaryl 7-ACA which otherwise would be discarded. Further, as the process is carried out in an aqueous medium, it does not require the transfer of the broth mixture to a solvent in order to accomplish the acetylation.

When R' is an acyl group and R is the "residue of a carboxylic acid", this includes those 7-position side chains known in the cephalosporin art and those 6-position side chains known in the penicillin art. Normally, these side chains are those in which R is the residue of a $C_1$–$C_{20}$ carboxylic acid, and are exemplified when R is hydrogen, $C_1$–$C_6$ alkyl, $C_1$–$C_6$ alkyl substituted by cyano, carboxy, halogen, amino, $C_1$–$C_4$ alkoxy, $C_1$–$C_4$ alkylthio, trifluoromethyl or trifluoromethylthio; naphthyl, phenyl or substituted phenyl group of the formula

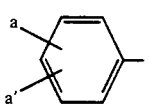

wherein a and a' independently are hydrogen, halogen, cyano, nitro, hydroxy, $C_1$–$C_4$ alkoxy, $C_1$–$C_4$ alkanoyloxy, $C_1$–$C_4$ alkyl, $C_1$–$C_4$ alkylthio, amino, $C_1$–$C_4$ alkanoylamino, $C_1$–$C_4$ alkylsulfonylamino, carboxy, carbamoyl, hydroxymethyl, aminomethyl, or carboxymethyl; a group of the formula

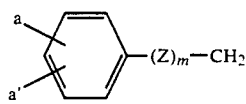

wherein a and a' have the same meanings as defined above, Z is O or S, and m is 0 or 1; an arylmethyl group of the formula

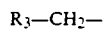

wherein $R_3$ is naphthyl, thienyl, furyl, benzothienyl, benzoaminothiazolyl, benzofuryl, pyridyl, 4-pyridylthio, pyrimidyl, pyridazinyl, indolyl, pyrazolyl, imidazolyl, triazolyl, tetrazolyl, oxazolyl, thiazolyl, oxadiazolyl, thiadiazolyl, and said arylmethyl groups substituted by amino, hydroxy, cyano, nitro, halogen, $C_1$–$C_4$ alkyl, $C_1$–$C_4$ alkyoxy, phenyl or substituted phenyl or $C_1$–$C_4$ alkylsulfonylamino; a substituted methyl group of the formula

wherein $R_4$ is cyclohex-1,4-dienyl, a phenyl or substituted phenyl of the formula

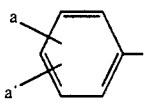

wherein a and a' are as defined above, or $R_4$ is $R_3$ as defined above, and Q is hydroxy, $C_1$–$C_4$ alkanoyloxy, carboxy, sulfo, amino, sulfoamino, or a substituted amino group of the formula

wherein $R^x$ is hydrogen or $C_1$–$C_3$ alkyl, $R^y$ is $C_1$–$C_4$ alkyl, furyl, thienyl, phenyl, halophenyl, nitrophenyl, styryl, halostyryl, nitrostyryl or a group of the formula

wherein $R^x$ has the same meanings as defined above and $R^z$ is hydrogen, $C_1$–$C_3$ alkylsulfonyl, $C_1$–$C_3$ alkyl, or $C_1$–$C_4$ alkanoyl; or Q is a substituted amino group of the formula

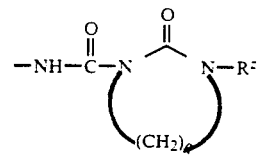

wherein $R^z$ has the same meaning as defined above, and q is 2 or 3; or Q is a substituted amino group of the formula

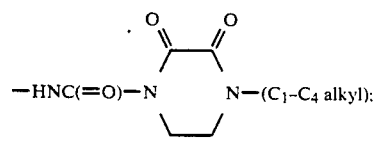

or Q is a benzamido group of the formula

wherein x is 1 to 3;
or Q is a pyridone or pyridonyl-carbonylamino group of the formula

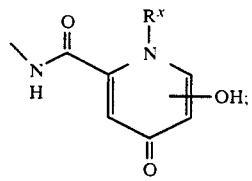

wherein $R^x$ is as defined above; or Q is a pyridylcarbonylamino group of the formula

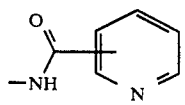

said group optionally substituted by $C_1$–$C_4$ alkyl, amino, carboxy, hydroxy or halogen; or Q is an imidazolyl or pyrazolyl group of the formula

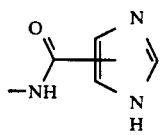

or

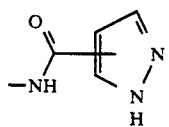

and said imidazolyl or pyrazolyl optionally substituted by $C_1$–$C_4$ alkyl, carboxy, amino or halogen; or Q is a benzpyridazin-4-one group or tautomer thereof represented by the formula

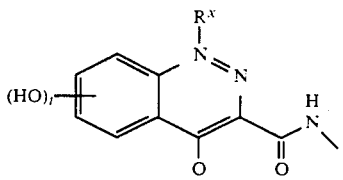

or

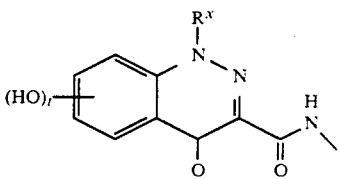

wherein $R^x$ is as defined above, and t is 1 to 3; or Q is a benzpyranone group of the formula

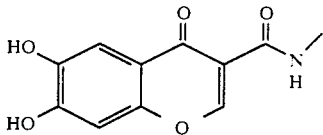

or R is a group of the formula

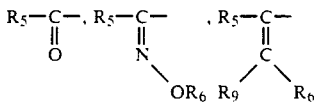

wherein $R^5$ is $R_3$ or $R_4$ as defined above, $R_9$ is hydrogen or halogen, and $R_6$ is hydrogen, $C_1$-$C_4$ alkyl, $C_1$-$C_4$ alkyl substituted by halogen, a carboxy-substituted alkyl or cycloalkyl group represented by the formula

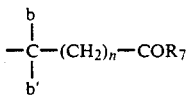

wherein b and b' independently are hydrogen or $C_1$-$C_3$ alkyl; n is 0, 1, 2, or 3; or b and b' when taken together with the carbon to which they are bonded form a 3- to 6-membered carbocyclic ring; and $R_7$ is hydroxy, $C_1$-$C_4$ amino, $C_1$-$C_4$ alkylamino, or di($C_1$-$C_4$ alkyl)amino; or $R_6$ is $C_1$-$C_4$ substituted by phenyl or phenyl substituted by one or two of the same or different groups selected from among $C_1$-$C_4$ alkyl, hydroxy, halogen, carboxy or protected carboxy; or $R_6$ is $C_1$-$C_4$ alkyl substituted by amino or protected amino; or $R_6$ is $C_1$-$C_4$ alkenyl; or $R_6$ is a cyclic lactam group of the formula

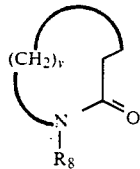

wherein:
v is 2–4 and
$R_8$ is hydrogen or $C_1$-$C_3$ alkyl; or
$R_6$ is an aryl methyl group of the formula $$R_3\text{—}CH_2\text{—}$$

wherein $R_3$ has the same meaning as defined hereinabove; or
R is a group of the formula $$\text{—}(CH_2)_t COOH$$

wherein t is as defined previously; or
R is a group of the formula $$\text{—}(CH_2)_t\overset{NH_2}{\underset{|}{C}}HCOOH$$

wherein t is as defined above; or
R is a group of the formula $$\text{—}(CH_2)_t\overset{R_{12}NR_{11}}{\underset{|}{C}}HCOOH$$

wherein t is as defined above, $R_{12}$ is hydrogen and $R_{11}$ is phenyl, substituted phenyl, or a group of the formula

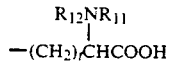

wherein $R_{13}$ may be phenyl, Substituted phenyl, $C_1$-$C_6$ alkyl, $C_1$-$C_6$ substituted alkyl, aminophenyl, phenylsulfonyl, (substituted phenyl)sulfonyl, $C_1$-$C_4$ alkoxy, or oxo($C_1$-$C_6$ alkyl).

In the above definition of the compounds represented by the Formula I, "$C_1$-$C_6$ alkyl refers to the straight and branched chain alkyl groups such as methyl, ethyl, n-propyl, isopropyl, n-butyl, s-butyl t- butyl, n-pentyl, n-hexyl, 3-methylpentyl, and like alkyl groups; $C_1$-$C_6$ substituted alkyl includes those $C_1$-$C_6$ alkyls substituted with cyano, carboxy, halogen, amine, $C_1$-$C_4$ alkoxy, $C_1$-$C_4$ alkylthio, trifluoromethyl, and trifluoromethylthio; "$C_1$-$C_6$ alkyl substituted by cyano" refers to cyanomethyl, cyanoethyl, 4-cyanobutyl, and the like; "$C_1$-$C_6$ alkyl substituted by ... carboxy" refers to such groups as carboxymethyl, 2-carboxyethyl, 2-carboxypropyl, 4-carboxybutyl, 5-carboxypentyl, and the like; "$C_1$-$C_6$ alkyl substituted by ... halogen" refers to chloromethyl, bromomethyl, 2-chloroethyl, 1-bromoethyl, 4-chlorobutyl, 4-bromopentyl, 6-chlorohexyl, 4-fluorobutyl, 3-fluoropropyl, fluoromethyl, and the like; "$C_1$-$C_6$ alkyl substituted by ... amino refers to such groups as 2-aminoethyl, aminomethyl, 3-aminopropyl and 4-aminobutyl; "$C_1$-$C_6$ alkyl substituted by ... $C_1$-$C_4$ alkoxy" refers to methoxy-methyl, 2-methoxyethyl, 2-ethoxyethyl, ethoxymethyl, 3-propoxypropyl, 3-ethoxybutyl, 4-t-butoxybutyl, 3-methoxy-pentyl, 6-methoxyhexyl, and like groups; $C_1$–$C_6$ alkyl substituted by . . . $C_1$–$C_4$ -alkylthio" refers to such groups as for example methylthiomethyl, 2-methylthioethyl, 2-ethylthiopropyl, 4-methylthiobutyl, 5-ethylthiohexyl, 3-t-butylthiopropyl, and like groups; "$C_1$–$C_6$ alkyl substituted by . . . trifluoromethyl" is exemplified by 2,2,2-trifluoroethyl, 3,3,3-trifluoropropyl, 4,4,4-trifluorobutyl, 6,6,6-trifluorohexyl, and the like; and "$C_1$–$C_6$ alkyl substituted by . . . trifluoromethylthio" refers to, for example, trifluoromethylthiomethyl, 2-trifluoromethylthioethyl, 2-trifluoromethylthiopropyl, 4-trifluoromethylthiobutyl, 5-trifluoromethylthiohexyl, and like $C_1$–$C_6$ alkyl substituted groups.

The term "$C_2$–$C_6$ alkenyl" denotes groups possessing between two and six carbon atoms and at least one double carbon-carbon bond. A few examples of such groups are vinyl, 1-propene-2-yl, 1-butene-4-yl, 1-pentyne-5-yl, 1-butyne-1-yl, and like groups.

The term "$C_2$–$C_6$ substituted alkenyl" denotes groups possessing between two and six carbon atoms, at least one double carbon-carbon bond, and substituted with one or more of halo, carboxy, amino, $C_1$–$C_4$ alkoxy, $C_1$–$C_4$ alkylthio, trifluoromethyl, trifluoromethylthio, cyano, and the like.

The term "$C_1$–$C_4$ alkylthio" refers to those groups possessing one to four carbon atoms and substituted with at least one sulfur atom.

The terms "halo" and "halogen" refer to the fluoro, chloro, bromo or iodo groups.

In the Formula I, substituted phenyl groups wherein the substituent(s) are represented by a and a' are exemplified by such groups as halophenyl such as 4-chlorophenyl, 3-bromophenyl, 2-fluorophenyl, 2-iodophenyl, 2,4-dichlorophenyl, and 3,5-di-chlorophenyl; hydroxyphenyl such as 2-hydroxyphenyl, 3-hydroxy-phenyl, 4-hydroxyphenyl, 2,4-dihydroxyphenyl, and 3,4-dihydroxy-phenyl; alkoxyphenyl, such as 2,6-dimethoxyphenyl, 4-methoxy-phenyl, 3-ethoxyphenyl, 3,4-dimethoxyphenyl, 4-t-butoxyphenyl, 4-methoxy-3-ethoxyphenyl, and 4-n-propoxyphenyl; alkanoyloxyphenyl such as 2-acetoxyphenyl, 4-propionoxyphenyl, 4-formyl-oxyphenyl, 4-acetoxyphenyl, 3-butyryloxyphenyl, and 3-acetoxy-phenyl; alkylphenyl such as 4-methylphenyl, 2-methylphenyl, 2,4-dimethylphenyl, 3-t-butylphenyl, 4-ethylphenyl, 4-ethyl-3-methylphenyl, and 3,5-dimethylphenyl; alkylthiophenyl such as 4-methylthiophenyl, 3-n-butylthiophenyl, 2-ethylthiophenyl, 3,4-dimethylthiophenyl, and 3-n-propylthiophenyl; aminophenyl such as 2-aminophenyl, 4-aminophenyl, 3,5-diaminophenyl, and 3-aminophenyl; alkanoylaminophenyl such as 2-acetylaminophenyl, 4-acetylaminophenyl, 3-propionylaminophenyl, and 4-butyrylaminophenyl; alkylsulfonylaminophenyl such as 3-methylsulfonylaminophenyl, 4-methylsulfonylaminophenyl, 3,5-di(methylsulfonylamino)phenyl, 4-n-butylsulfonylaminophenyl, and 3-ethylsulfonylaminophenyl; carboxyphenyl such as 2-, 3-, or 4-carboxyphenyl, 3,4-dicarboxyphenyl, and 2,4-dicarboxyphenyl; carbamoylphenyl such as 2-carbamoylphenyl, 2,4-dicarbamoylphenyl, and 4-carbamoylphenyl; hydroxymethylphenyl such as 4-hydroxymethylphenyl and 2-hydroxymethylphenyl; aminomethylphenyl such as 2-aminomethylphenyl and 3-aminomethylphenyl; and carboxymethylphenyl such as 2-carboxymethylphenyl, 4-carboxymethylphenyl, and 3,4-di(carboxymethyl)phenyl; and the substituted phenyl groups bearing different substituents such as 4-chloro-3-methylphenyl, 4-fluoro-3-hydroxyphenyl, 3,5-dichloro-4-hydroxyphenyl, 4-hydroxy-3-chlorophenyl, 4-hydroxy-3-methylphenyl, 4-ethyl-3-hydroxyphenyl, 4-methoxy-3-hydroxyphenyl, 4-t-butyloxy-2-hydroxyphenyl, 4-acetylamino-3-methoxyphenyl, 3-amino-4-ethylphenyl, 2-aminomethyl-4-chlorophenyl, 2-hydroxymethyl-3-methoxyphenyl, 2-hydroxymethyl-4-fluorophenyl, 2-acetoxy-4-aminophenyl, 4-acetoxy-3-methoxyphenyl, 3-isopropylthio-4-chlorophenyl, 2-methylthio-4-hydroxymethylphenyl, 4-carboxy-3-hydroxyphenyl, 4-ethoxy-3-hydroxyphenyl, 4-methylsulfonylamino-2-carboxyphenyl, 4-amino-3-chlorophenyl, and 2-carboxy-methyl-4-hydroxyphenyl.

Examples of RCO- groups of the Formula I wherein R is a group represented by the formula

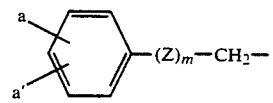

with m=0 are: phenylacetyl, 4-hydroxyphenylacetyl, 4-chloro-phenylacetyl, 3,4-dichlorophenylacetyl, 4-methoxyphenylacetyl, 3-ethoxyphenylacetyl, 2-aminomethylphenylacetyl, 3-carboxy-phenylacetyl, 4-acetoxyphenylacetyl, 3-aminophenylacetyl, and 4-acetylaminophenylacetyl; and with m=1 and Z=0, phenoxy-acetyl, 4-chlorophenoxyacetyl, 4-fluorophenoxyacetyl, 3-aminophenoxyacetyl, 3-hydroxyphenoxyacetyl, 2-methoxyphenoxyacetyl, 2-methylthiophenoxyacetyl, 4-acetylaminophenoxyacetyl, 3,4-dimethylphenoxyacetyl, and 3-hydroxymethyl-phenoxyacetyl; and with m=1 and Z=S, phenylthioacetyl, 4-chlorophenylthioacetyl, 3,4-dichlorophenylthioacetyl, 2-fluoro-phenylthioacetyl, 3-hydroxyphenylthioacetyl, and 4-ethoxyphenylthioacetyl.

Examples of $R_3$—$CH_2CO$— groups of the Formula I wherein $R_3$ is a heteroaryl group are: 2-thienylacetyl, 3-thienylacetyl, 2-furylacetyl, 2-benzothienylacetyl, 2-benzo-furylacetyl, indol-2-ylacetyl, 1H-tetrazol-1-ylacetyl, oxazol-2-ylacetyl, oxazol-4-ylacetyl, thiazol-4-ylacetyl, 2-aminothiazol-4-ylacetyl, 1,3,4-oxadiazol-2-ylacetyl, 1,3,4-thiadiazol-2-yl-acetyl, 5-ethyl-1,3,4-thiadiazol-2-ylacetyl, and like heteroaryl groups substituted by amino, $C_1$–$C_4$ alkylsulfonylamino, hydroxy, halo, $C_1$–$C_4$ alkyl or $C_1$–$C_4$ alkoxy groups.

Examples of RCO— groups of the Formula I compounds wherein R is a substituted methyl group represented by the formula $R_4$—$CH(Q)$— and Q is amino, carboxy, hydroxy, or sulfo, are 2-carboxy-2-phenylacetyl, 2-amino-2-(2-naphthalenyl)acetyl, 2-carboxy-2-(4-hydroxyphenyl)acetyl, 2-amino-2-phenylacetyl, 2-amino-2-(4-hydroxyphenyl)acetyl, 2-amino-2-(3-chloro-4-hydroxyphenyl)acetyl, 2-amino-2-(cyclohex-1,4-dien-1-yl)-acetyl, 2-amino-2-(3-methylsulfonamidophenyl)acetyl, 2-amino-2-(3-ethylsulfonaminophenyl)acetyl, 2-hydroxy-2-phenylacetyl, 2-formyloxy-2-phenylacetyl, 2-sulfo-2-phenylacetyl, 2-sulfo-2-(4-methylphenyl)acetyl, and 2-acetoxy-2-(3-hydroxyphenyl)acetyl, 2-amino-2-(2-thienyl)acetyl, 2-amino-2-(3-benzothienyl)acetyl, 2-amino-2-(1H-tetrazol-1-yl)acetyl, 2-hydroxy-2-(1,3,4-thiadiazol-2-yl)acetyl, 2-amino-2-(2-aminothiazol-4-yl)acetyl, 2-carboxy-2-(2-thienyl)acetyl, 2-carboxy-2-(benzo-thien-2-yl)acetyl, and 2-hydroxy-2-(benzofur-2-yl)acetyl; and when Q is a substituted amino group represented by the formula

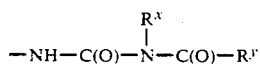

examples of such acyl groups are 2-(N-methyl-N-benzoyl-carbamoylamino)-2-phenylacetyl, 2-(N-methyl-N-cinnamoylcarbamoylamino)-2-(2-furyl)acetyl, 2-(N,N-dimethylcarbamo-ylureido)-2-(4-chlorophenyl)acetyl, 2-[N-methyl-N-(2-chloro-cinnamoyl)carbamoylamino]-2-(2-thienyl)acetyl, and 2-(N-ethyl-N-acetylcarbamoylamino)-2-(4-hydroxyphenyl)acetyl; and when Q is a substituted amino group represented by the formula

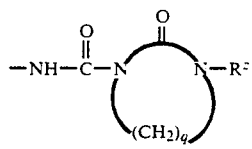

examples are 2-[(3-methylimidazolidin-2-one-1-yl)carbonylamino]-2-phenylacetyl, 2-[(3-acetylimidazolidin-2-one-1-yl)carbonylamino]-2-phenylacetyl, 2-[(3-methylsulfonylimidazolidin-2-one-1-yl)-2-(2-thienyl)acetyl, and 2-[(3-acetylhexahydropyrimidin-2-one-1-yl)carbonylamino]-2-phenylacetyl; and when Q is a hydroxy-substituted benzamido group represented by the formula

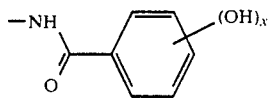

examples of such acyl groups are 2-(2,4-dihydroxybenzamido)-2-phenylacetyl, 2-(4-hydroxybenzamido)-2-(4-hydroxyphenyl)-acetyl, 2-(3,4-dihydroxybenzamido)-2-(2-aminothiazol-4-yl)-acetyl, 2-(3,5-dihydroxybenzamido)-2-(3-thienyl)acetyl, and 2-(2-hydroxybenzamido)-2-(2-benzofuryl)acetyl.

When Q is an hydroxy-substituted pyridinecarbonylamino group, examples include e.g., 2-hydroxy-pyridin-4-one-6-ylcarbonylamino and 3-hydroxypyridin-4-one-6-ylcarbonylamino. When Q is a pyridylcarbonylamino group examples are e.g., pyridin-3-ylcarbonylamino, 4-aminopyridin-3-ylcarbonylamino, 5-chloropyridin-2-ylcarbonylamino, 3-carboxypyridin-4-yl-carbonylamino, and 4-aminopyridino-2-ylcarbonylamino. When Q is an imidazole or pyrazole group as defined above examples include e.g., 2-aminoimidazol-4-ylcarbonylamino, 5-carboxy-2-methylimidazol-4-ylcarbonylamino, 5-carboxypyrazol-3-yl-carbonylamino, 3-aminopyrazol-4-ylcarbonylamino and 4-hydroxypyrazol-5-ylcarbonylamino. When Q is a benzpyridazin-4-one-3-ylcarbonylamino group, examples of Q are represented by the formulae

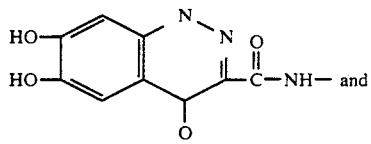

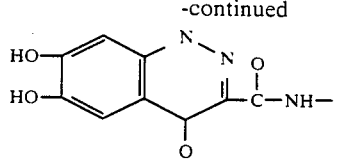

Examples of RCO acyl groups of the compounds represented by Formula I when R is a keto group or an oximino-substituted group represented by the formulae

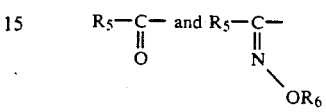

are the keto groups 2-oxo-2-phenylacetyl, 2-oxo-2-(2-thienyl)-acetyl, 2-oxo-2-(2-aminothiazol-4-yl)acetyl; and oximino-substituted groups 2-phenyl-2-methoxyaminoacetyl, 2-(2-thienyl)-2-ethoxyiminoacetyl, 2-(2-furyl)-2-methoxyimino-acetyl, 2-(2-benzothienyl)-2-carboxymethoxyiminoacetyl, 2-(2-thienyl)-2(2-carboxyethoxy)iminoacetyl, 2-(2-amino-1,2,4-thiadiazol-4-yl)-2-methoxyiminoacetyl, 2-(2-aminothiazol-4-yl)-2-methoxyiminoacetyl, 2-(2-chlorothiazol-4-yl)-2-methoxyiminoacetyl, 2-(2-aminothiazol-4-yl)-2-(2-carboxyprop-2-yl)oxyiminoacetyl, 2-(2-aminothiazol-4-yl)-2-(2-carbamoyl-prop-2-yl)oxyiminoacetyl, 2-(5-amino-1,3,4-thiadiazol-2-yl)-2-methoxyiminoacetyl.

When $R_6$ of formula (1) is $C_1$–$C_4$ alkyl substituted by phenyl or substituted phenyl, such groups are exemplified by benzyl, 4-hydroxybenzyl, 4-chlorobenzyl, 3-carboxybenzyl, 3-chloro-4-hydroxybenzyl, 2-phenylethyl, 1-phenylethyl, 3-phenyl-propyl, 4-hydroxy-2-phenylpropyl, 3-phenylbutyl and like phenyl-alkyl groups.

When $R_6$ represents $C_1$–$C_4$ alkyl substituted by amino or protected amino, examples include 2-aminoethyl, 3-aminopropyl, 4-aminobutyl, 2-aminopropyl and such groups wherein the amino group is protected by an amino-protecting group.

When $R_6$ is a $C_2$–$C_4$ alkenyl group, examples include allyl, butene-2, butene-3, butene-1, and like groups.

Examples of the compounds represented by formula (1) when R is a group of the formula

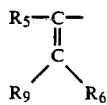

may be found in Hamashima, U.S. Pat. No. 4,634,617 incorporated herein by reference. Exemplary substituents are, for $R_9$, hydrogen, for $R_5$, phenyl, furyl, thienyl, oxazolyl, isoxazolyl, optimally protected aminoisoxazolyl, thiazolyl, optionally protected aminothiazolyl, thiadiazolyl, and aminothiazolyl, and for $R_6$, $C_1$–$C_3$ alkenyl and —$CH_2COO_2H$.

When R is a group of the formula

—$(CH_2)_rCH(R_{12}NR_{11})COOH$ examples of $R_{11}$, when $R_{12}$ is hydrogen, include:

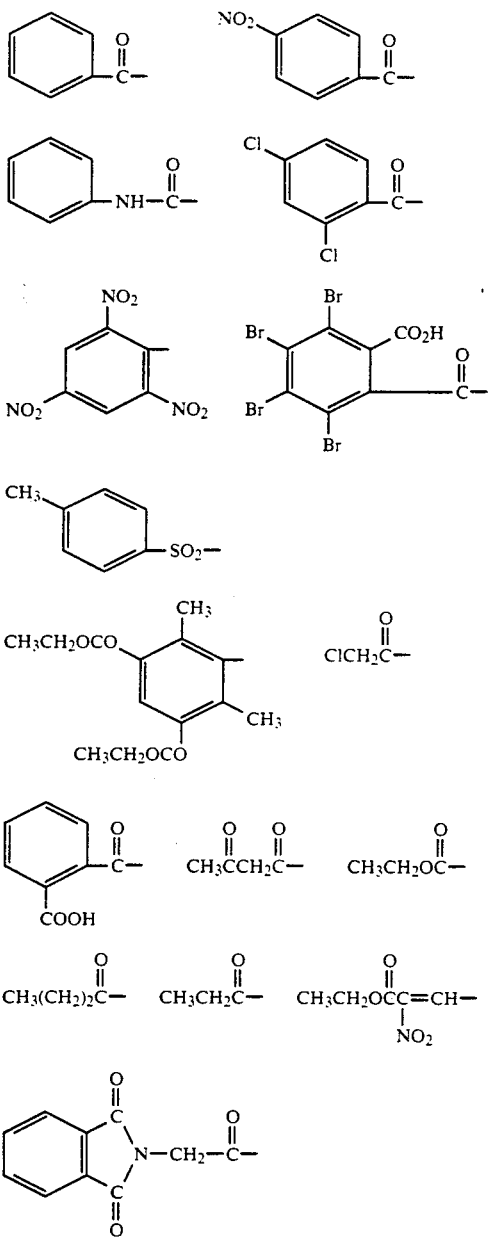

or $R_{11}$ and $R_{12}$ may together form the group

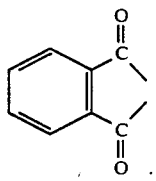

Further Examples of such $R_{11}$ and $R_{12}$ groups may be found in the following U.S. Pat. Nos.: 3,853,863; 3,522,248; 3,573,296; 3,641,018; 3,980,644; and 3,821,208; in the following Japanese Patent Nos.: 108,085 (1976); 112,892 (1978); 53,689 (1978); 029,493 (1976); 13,389 (1973); 149,694 (1975); 82,791 (1977); in the following German Patent Nos.: 2,157,693; 2,721,731; 2,507,117; 2,208,631; 2,458,554; 2,418,088; 2,523,280; and 2,841,363; in the Belgium Patent No. 796,540 (1973); in the British Patent Nos. 1,565,053 and 2,040,942; and in the following article: Andrisano, R. et al., J. Appl. Chem. Biotechnol, (1976), 26, 459–468; all of the above being herein incorporated by reference.

The term "carboxy-protecting group" as used in this document refers to conventional groups commonly used in the β-lactam art to block or protect the carboxylic acid group while reactions are carried out on other functional groups on the compound. Examples of such carboxylic acid protecting groups include benzyl, 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, t-butyl, t-amyl, trityl, 4-methoxytrityl, 4,4'-dimethoxytrityl, 4,4', 4'''-trimethoxytrityl, 2-phenylprop-2-yl, trimethylsilyl, t-butyldimethylsilyl, phenacyl, 2,2,2-tri-chloroethyl, 2-(trimethylsilyl)ethyl, 2-(di(n-butyl)methylsilyl)-ethyl, 2-(p-toluenesulfonyl)ethyl, 2-(4-nitrobenzylsulfonyl)ethyl, allyl, cinnamyl, 1-(trimethylsilylmethyl)prop-1-en-3-yl, and like moieties. The species of carboxy-protecting group employed is not critical so long as the derivatized carboxylic acid is stable to the conditions of subsequent reaction(s) on other positions of the molecule and can be removed at the appropriate point without disrupting the remainder of the molecule. In particular, it is important not to subject the carboxy-protected 1-carba-cephalosporin molecule to strong nucleophilic bases. Such harsh removal conditions are also to be avoided when removing amino-protecting groups, discussed below. Preferred carboxylic acid protecting groups are the benzhydryl, allyl and p-nitrobenzyl groups. Carboxy-protecting groups similar to those used in the cephalosporin, penicillin and peptide arts can also be used to protect a carboxy group substituents of the compounds provided herein. Further examples of these groups are found in E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5.

The term "amino-protecting group" as used in the specification refers to substituents of the amino group commonly employed to block or protect the amino functionality while reacting other functional groups on the compound. Examples of such amino-protecting groups include the formyl group, the trityl group, the phthalimido group, the trichloroacetyl group, the chloroacetyl, bromoacetyl and iodoacetyl groups, urethane-type blocking groups such as benzyloxycarbonyl, 4-phenylbenzyloxy-carbonyl, 2-methylbenzyloxycarbonyl, 4-methoxybenzyloxy-carbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 1,1-diphenyleth-1-yloxycarbonyl, 1,1-diphenylprop-1-yloxycarbonyl, 2-phenylprop-2-yloxycarbonyl, 2-(p-toluyl)prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)ethoxycarbonyl, 2-(methylsulfonyl)ethoxycarbonyl, 2-(triphenylphosphino)-ethoxycarbonyl, 9-fluorenylmethoxycarbonyl ("FMOC"), 2-(trimethylsilyl)ethoxy-carbonyl, allyloxycarbonyl, 1-(trimethylsilylmethyl)prop-1-en-3-yloxycarbonyl, 4-acetoxybenzyloxycarbonyl, 2,2,2-trichloro-ethoxycarbonyl, 2-ethynyl-2-propoxycarbonyl, cyclopropyl-methoxycarbonyl, 4-(decyloxy)benzyloxycarbonyl, 1-piperidyloxy-carbonyl and the like; the benzoylmethylsulfonyl group, the 2-(nitro)phenylsulfonyl group, the diphenylphosphine oxide group and like amino-protecting groups. The species of amino-protecting group employed is not critical so long as the derivatized amino group is stable to the condition of subsequent reaction(s) on other positions of the molecule and can be removed at the appropriate point without disrupting the remainder of the molecule. Preferred amino-protecting groups are the 1,2-bis(dimethylsilyl)ethylene (See, e.g., U.S. Pat. No. 4,558,124), benzyloxycarbonyl, p-nitrobenzyloxycarbonyl, allyloxycarbonyl, t-butoxycarbonyl, and trityl groups. Similar amino-protecting groups used in the cephalosporin, penicillin and peptide art are also embraced by the above terms. Further examples of groups referred to by the above terms are described by J. W. Barton, "Protective Groups In Organic Chemistry", J. G. W. McOmie, Ed., Plenum Press, New York, N.Y., 1973, Chapter 2, and T. W. Greene, "Protective Groups in Organic Synthesis", John Wiley and Sons, New York, N.Y., 1981, Chapter 7.

A preferred compound is represented when R' is an acyl group

wherein R is of the formula —(CH$_2$)$_3$COOH; and R$_2$ is hydrogen.

The particular base employed in the process must be able, under aqueous conditions, to form a salt with the acid by-product of the anhydride, thereby effectively neutralizing the acid by-product sufficiently to allow the reaction to proceed. Preferably, the base will maintain a pH of the reaction between 7-11. The base also should be chosen so as to not result in a competing reaction between it and the anhydride to the exclusion of the acetylation process.

Such bases, for example, include inorganic hydroxides, and inorganic phosphates. Also, tri(C$_1$-C$_4$ alkyl) amines have been found to satisfy the requirements for the process. Particularly, bases include sodium hydroxide, potassium hydroxide, calcium hydroxide, magnesium hydroxide, sodium phosphate, potassium phosphate, calcium phosphate, and triethylamine. Sodium hydroxide, potassium hydroxide and sodium phosphate are preferred, with sodium hydroxide being most preferred.

The acid anhydrides used are of the general formula

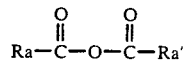

wherein Ra and Ra' may independently be C$_1$-C$_6$ alkyl, C$_2$-C$_6$ alkenyl, C$_1$-C$_4$ alkylbenzene groups such as benzyl and phenethyl, or aryl groups such as phenyl and tolyl. Further, the groups of Ra and Ra' may be substituted 1 to 4 times with C$_1$-C$_6$ alkyl, C$_2$-C$_6$ alkenyl, halogen, nitro, amido or carbonyl groups. The term aryl group is defined to include those univalent groups derived from monocyclic arenes by conceptual removal of one hydrogen atom from a carbon atom of the ring.

The term "residue of an anhydride" is defined to be the same as Ra or Ra', and, of course, is directly related to the particular acid anhydrides as herein described, used in the process.

While both symmetrical and unsymmetrical anhydrides may be used, symmetrical anhydrides are preferred. The following list provides examples of such anhydrides: acetic anhydride, butyric anhydride, heptanoic anhydride, pivalic anhydride, propionic anhydride, benzoic anhydride, phenylacetic anhydride, crotonic anhydride, chloroacetic anhydride, dichloroacetic anhydride and trifloroacetic anhydride.

The preferred anhydride is acetic anhydride. It is preferable to use a stoichmetric excess (above 1:1) of the anhydride, 10-20 molar equivalents being most preferred.

The reaction may be run at temperatures between about −10° C. to about 40° C., with the preferred range being between about 0° to about 10° C. Further, the pH of the reaction should be in the range of 7 to about 11, with a pH of about 9 to about 10.5 being preferred.

The concentrates of the substrate should preferably above 10%.

The following illustrates the reaction Scheme of the present invention.

SCHEME

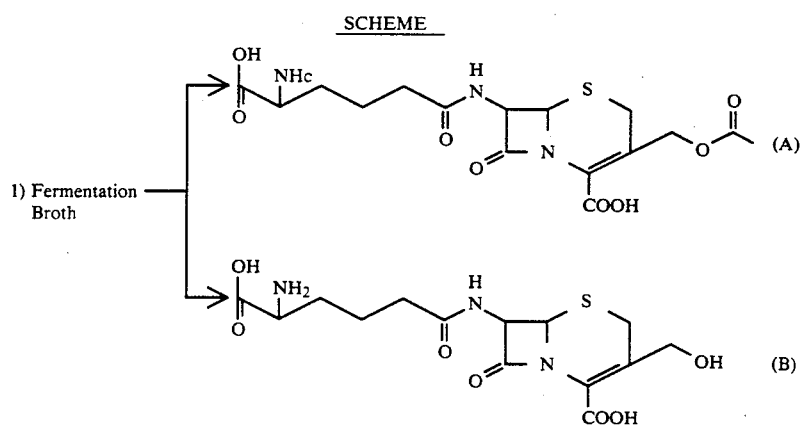

SCHEME
-continued

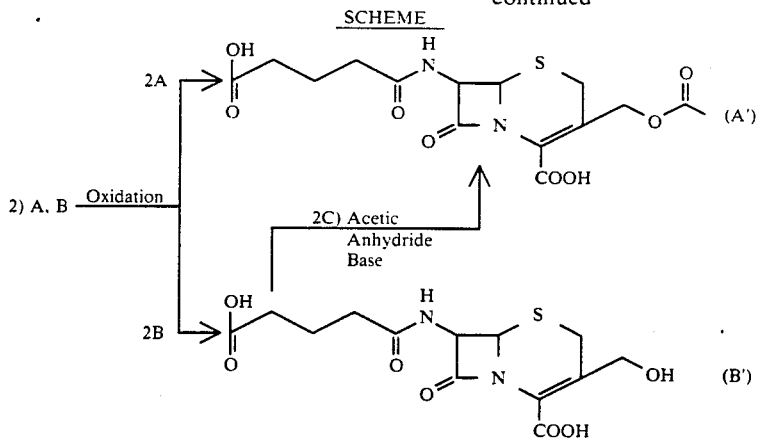

In the above Scheme it is noted that from the fermentation broth, compound A (Cephalosporin C) and compound B (desacetyl cephalosporin C) are present. In step 2, both A and B undergo an oxidation reaction as previously discussed. In step 2A, compound A' (glutaryl 7-ACA) is formed while in 2B, compound B' (desacetyl glutaryl 7-ACA) is formed. Compound B' is acetylated in an aqueous medium by reacting it with acetic anhydride base as previously described to form compound A'. A' then may undergo cleavage of the α-aminoadipyl side chain, which results in 7-ACA:

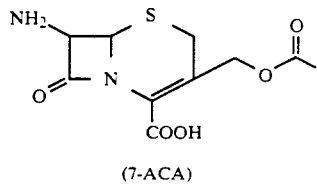

(7-ACA)

The Scheme is provided to illustrate the invention, it being understood that 3-acetylation may be performed on substrates having a 4-protected carboxy, a variety of 7-position sidechains, and by using different anhydrides, as herein described.

The following examples are used to illustrate the invention and are not meant to limit such.

EXAMPLES

Preparation I

Desacetyl Glutaryl 7ACA

A) Glutaryl 7ACA (3.0 g) is slurried in 45 ml water and the pH is adjusted to 6.0 with 20% sodium hydroxide to dissolve the glutaryl 7ACA. Yeast esterase (0.3 g) is added and the solution is stirred at 22°–25° C. for 4 hours while maintaining the pH at 5.9–6.1 with 20% sodium hydroxide. The yield by HPLC to desacetyl glutaryl 7ACA is 98% with the ratio of desacetyl glutaryl 7ACA to glutaryl 7ACA >99%. The resulting solution is filtered with filter aid to remove the yeast and aliquots are used for subsequent chemical conversions of desacetyl glutaryl 7ACA to glutaryl 7ACA. The solution may be stored frozen.

Desacetyl Glutaryl 7ACA Calcium Salt

A) Glutaryl 7ACA (4.0 g) is slurried in 60 ml water and the pH is adjusted to 3.5 to 4.0 with 20% sodium hydroxide to dissolve the glutaryl 7ACA. To the solution is added 2.2 g calcium chloride and the pH is adjusted to 5.5 to 6.0 with 20% sodium hydroxide. Yeast esterase (0.4 g) is added and the solution is stirred at 22°–25° C. for 2.5 hours while maintaining the pH at 5.9–6.1 with 20% sodium hydroxide. The yield by HPLC to desacetyl glutaryl 7ACA is 97% with the ratio of desacetyl glutaryl 7ACA to glutaryl 7ACA >99%. The resulting solution is filtered with filter aid to remove the yeast and is diluted with water to 90 ml. Desacetyl glutaryl 7ACA calcium salt is precipitated by the addition of 450 ml ethanol. The crystals are filtered, washed with ethanol, and dried. Subsequent crystals which come out in the filtrate are similarly filtered and dried. (Crystal purity as desacetyl glutaryl 7ACA is 63%). The crystallization yield is 83%. The desacetyl glutaryl 7ACA calcium salt was characterized by NMR and IR:

$^1$H-NMR (In D$_2$O): δ5.53(1H,d,J 4.6Hz,7-H),5.03(1H,d,J 4.7Hz,6-H), 3.37 and 3.56 (2H ABq J$_{AB}$ 17.8 Hz, S-CH$_2$,), and 4.17 and 4.20 (2H ABq JAB 12.9 Hz, CH$_2$-OH), 2.27 (2H, t, J 7.5 Hz, CH$_2$-CO), 2.14 (2H, t, J 7.5 Hz, CH$_2$-CO), and 1.77 (2H, m, J 7.6 Hz, —CH$_2$—).

IR (KBr) ν$_{max}$: 3379, 1757, 1557, 1416, 1114, 1071, 1037.

Experiment 1

Glutaryl 7ACA

A) To an aqueous solution of desacetyl glutaryl 7ACA (4 ml, 0.20 mmoles) chilled in an ice bath is added 0.4 ml acetic anhydride (4.2 mmoles) dropwise and 20% sodium hydroxide (9.75 mmoles) is pumped in to maintain the reaction pH at 7.0±1. After all of the acetic anhydride is added and the pH stabilizes, by HPLC there is now 0.148 moles of glutaryl 7ACA (yield is 74%). There is 4.5% of desacetyl glutaryl 7ACA remaining along with 10% of a compound tentatively identified as the cyclic glutarimide 7ACA derivative.

B) The reaction as described in (A) is run at pH 9 using 10 mmole sodium hydroxide for a 95% yield to glutaryl 7ACA with 6% desacetyl glutaryl 7ACA remaining and 1.8% of the "imide".

C) To an aqueous solution of desacetyl glutaryl 7ACA (3 ml, 0.28 mmoles) chilled in an ice bath is then added simultaneously 0.283 ml acetic anhydride (3 mmoles) at 0.1 mmole/min and 40% potassium hydroxide at a rate to maintain the reaction pH at 10.0±1 By HPLC after half the acetic anhydride is added approximately 53% of the desacetyl glutaryl 7ACA is converted to glutaryl 7ACA. After all of the acetic anhydride is added the pH is allowed to drift down to 8.2 and the reaction solution is diluted with water to 10 ml. The solution now contains 0.238 mmole glutaryl 7ACA (yield is 85%). There is 8% of desacetyl glutaryl 7ACA remaining along with 7% of a compound tentatively identified as the cyclic glutarimide 7ACA derivative.

D) To 500 ml oxidized resin eluate derived from ceph C broth and containing 9.56 g glutaryl 7ACA (26.7 mmole) and 1.30 g desacetyl glutaryl 7ACA (4.1 mmoles) is added 25 ml acetic anhydride (265 mmoles) over 32 minutes. During the addition the pH is controlled at 10.5±0.5 with 40% sodium hydroxide using a pH controller to activate the sodium hydroxide pump. At the end of the reaction the treated eluate now contained 10.59 g glutaryl 7ACA (29.5 mmoles) and 0.33 g desacetyl glutaryl 7ACA (1.0 mmoles). The glutaryl 7ACA/desacetyl glutaryl 7ACA ratio is increased from 87% to 97% and there is a 10% increase in the amount of glutaryl 7ACA present in the eluate.

E) To 4 ml oxidized resin eluate derived from ceph C broth and containing 0.123 g glutaryl 7ACA (0.34 mmole) and 0.027 g desacetyl glutaryl 7ACA (0.085 mmole) is added dropwise 0.2 ml acetic anhydride (2.1 mmole). During the addition the pH is controlled at 9.0±1 with triethylamine (0.48 ml, 3.45 mmole). At the end of the reaction the treated eluate now contains 0.128 g glutaryl 7ACA (0.36 mmoles) and 0.013 g desacetyl glutaryl 7ACA (0.04 mmoles). The glutaryl 7ACA/desacetyl glutaryl 7ACA ratio is increased from 80% to 90% and there is a 4% increase in the amount of glutaryl 7ACA present in the eluate.

F) To an aqueous solution of desacetyl glutaryl 7ACA (3 ml, 0.28 mmoles) chilled in an ice bath is added simultaneously 0.385 ml propionic anhydride (3 mmoles) at 0.1 mmole/min and 40% sodium hydroxide at a rate to maintain the reaction pH at 10.0±1. By HPLC, after half the propionic anhydride is added, approximately 53% of the desacetyl glutaryl 7ACA is converted to the 3'-propionyl derivative of glutaryl 7ACA. After all of the propionic anhydride is added the reaction solution is diluted with water to 10 ml. The yield to the glutaryl 7ACA 3'-propionyl derivative is 81%. There is 13% of desacetyl glutaryl 7ACA remaining.

G) To an aqueous solution of desacetyl glutaryl 7ACA (3 ml, 0.28 mmoles) chilled in an ice bath is added simultaneously 0.497 ml isobutyric anhydride (3 mmoles) at 0.1 mmole/min and 40% sodium hydroxide at a rate to maintain the reaction pH at 10.0±1. By HPLC, one hour after all of the isobutyric anhydride is added, about 26% of the desacetyl glutaryl 7ACA is converted to the 3'-isobutyryl derivative of glutaryl 7ACA.

Experiment 2

Glutaryl 7ACA Calcium Salt

A) 1.05 g desacetyl glutaryl 7ACA calcium salt (2.0 mmoles) is dissolved in 10 ml water and the solution is diluted to 15 ml with water. The solution is chilled in an ice bath and then added simultaneously is 1.9 ml acetic anhydride (20 mmoles) at 0.0475 ml/min and 40% sodium hydroxide at a rate to maintain the reaction pH at 10.0±1. By HPLC the >99% desacetyl glutaryl 7ACA/glutaryl 7ACA is converted to 97% glutaryl 7ACA/desacetyl glutaryl 7ACA. After all of the acetic anhydride is added the pH is allowed to drift down to 9.1 and 3.33 g calcium chloride is added which upon dissolving lowers the pH to 7.22. One drop of 6N HCl is added to drop the pH to 6.4 and the reaction solution is diluted with water to 25 ml. The conversion yield at this point by HPLC is 90%. The glutaryl 7ACA calcium salt product is precipitated by adding 10 volumes (250 ml) of ethanol to the reaction solution. A gelatinous precipitate of calcium acetate coprecipitates with the product. The precipitate is filtered and washed with 50 ml ethanol, then is dried at 50° C. in the vacuum oven. The dry powder is pulverized and reslurried in 250 ml methanol to dissolve the calcium acetate. The product is filtered and washed with 50 ml methanol. Crystallization yield to the air-dried powder (glutaryl 7ACA purity is 48%) is 93%. Besides HPLC identification, the product matches the starting NMR and IR spectra of glutaryl 7ACA.

$^1$H-NMR (in D$_2$O):Glutaryl 7ACA: δ5.53 (1H, d, J 4.7 Hz, 7-H), 5.03 (1H, d, J 4.7 Hz, 6-H), 3.32 and 3.58 (2H ABq J$_{AB}$ 17.9 Hz, S-CH), 4.64 and 4.80 (2H ABq J$_{AB}$ 12.4 Hz, CH2-OAc), 2.28 (2H, t, J 7.5 Hz, CH$_2$-CO), 2.15 (2H, t, J 7.6 Hz, CH$_2$-CO), 1.79 (2H, m, J 7.6 Hz, —CH$_2$—), and 2.02 (3H, s, Ac).

IR (KBr) V$_{max}$: 3386, 1761, 1558, 1417, 1237, 1118, 1073, 1039.

1H-NMR (in D$_2$O):Glutaryl 7ACA Derived from Desacetyl Glutaryl 7ACA: δ5.56 (1 H, d, J 4.8 Hz, 7-H), 5.03 (1 H, d, J 4.7 Hz, 6-H), 3.32 and 3.57 (2H ABq J$_{AB}$ 17.9 Hz, S-CH2). 4.63 and 4.79 (2H ABq JAB 12.4 Hz. CH$_2$-OAc) 2.26 (2H, t, J 7.5 Hz, CH$_2$-CO), 2.14 (2H, t, J 7.6 Hz, CH$_2$-CO), 1.78 (2H, m, J 7.6 Hz, —CH$_2$—), and 2.01 (3H, s, Ac).

IR (KBr) V$_{max}$ 3410, 1760, 1558, 1418, 1240, 1118, 1073, 1039.

I claim:

1. A process for the preparation of a compound of the formula

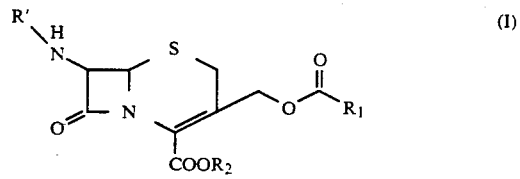

wherein
R$_1$ is the residue of an acid anhydride of the formula

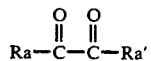

wherein R$_a$ and R$_a'$ may independently be C$_1$-C$_6$ alkyl, C$_2$-C$_6$ alkenyl, C$_1$-C$_4$ alkylbenzene, or acyl, and such groups substituted 1–4 times with C$_1$-C$_6$ alkyl, halogen, nitro, amide or carbonyl groups;
R$_2$ is hydrogen or a carboxy-protecting group; and
R' is hydrogen, an amino-protecting group, or an acyl group of the formula

where R is the residue of a carboxylic acid; which comprises reacting a compound of the formula

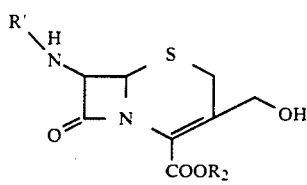

with an acid anhydride as defined above in the presence of a base selected from tri($C_1$-$C_4$ alkyl)amines, sodium hydroxide, potassium hydroxide, calcium hydroxide, magnesium hydroxide, sodium phosphate, potassium phosphate and calcium phosphate in an aqueous solution.

2. The process as recited in claim 1 wherein R' is a group of the formula

wherein R is a group of the formula

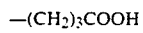

3. The process as recited in claim 1 wherein $R_2$ is hydrogen.

4. The process as recited in claim 1 wherein said anhydride is one selected from the group consisting of acetic anhydride, butyric anhydride, heptanoic anhydride, pivalicanhydride, propionic anhydride, benzoic anhydride, phenylacetic anhydride, crotonic anhydride, chloroacetic anhydride, dichloroacetic anhydride and trifluoroacetic anhydride.

5. The process as recited in claim 4 wherein said anhydride is acetic anhydride.

6. The process as recited in claim 1 wherein said anhydride is present in the amount of about 10 to 20 molar equivalents to the compound of Formula II.

7. The process as recited in claim 1 wherein the reaction temperature is maintained at between about $-10°$ C. to about 40° C.

8. The process as recited in claim 7 wherein said temperature is maintained at between about 0° C. to about 10° C.

9. The process as recited in claim 1 wherein the pH of the reaction is maintained between about 7 to about 11.

10. A process for the preparation of a compound of the formula

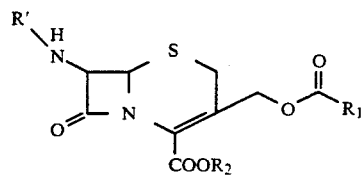

wherein
$R_1$ is the residue of an acid anhydride of the formula

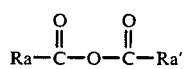

wherein Ra and Ra' may independently be $C_1$-$C_6$ alkyl, $C_2$-$C_6$ alkenyl, $C_1$-$C_4$ alkylbenzene, or aryl, and such groups substituted 1-4 times with $C_1$-$C_6$ alkyl, halogen, nitro, amide or carbonyl groups;
$R_2$ is hydrogen or a carboxy-protecting group; and
R' is hydroxy, amino-protecting group, or an acyl group of the formula

where R is the residue of a carboxylic acid; which comprises reacting a compound of the formula

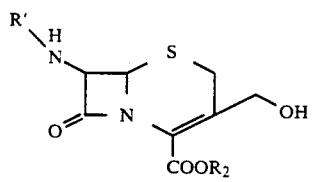

with an acid anhydride, as herein before described, in the presence of a base selected from the group of sodium hydroxide, potassium hydroxide or sodium phosphate, in an aqueous solution.

11. The process as recited in claim 10 wherein $R_1$ is an acyl group wherein R is a group of the formula

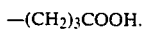

12. The process as recited in claim 10 wherein $R_2$ is hydrogen.

13. The process as recited in claim 10 wherein said anhydride is one selected from the group consisting of acetic anhydride, butyric anhydride, heptanoic anhydride, pivalicanhydride, propionic anhydride,benzoic anhydride, phenylacetic anhydride, crotonic anhydride, chloroacetic anhydride, dichloroacetic anhydride and trifluoroacetic anhydride.

14. The process as recited in claim 13 wherein said anhydride is acetic anhydride.

15. The process as recited in claim 14 wherein said anhydride is present in the amount of about 10 to 20 molar equivalents to the compound of Formula II.

16. The process as recited in claim 10 wherein the reaction temperature is maintained at between about $-10°$ C. to about 40° C.

17. The process as recited in claim 16 wherein said temperature is maintained at between about 0° C. to about 10° C.

18. The process as recited in claim 10 wherein the pH of the reaction is maintained between about 7 to about 11.

19. The process as recited in claim 18 wherein the pH is maintained between about 9 and about 10.5.

20. A process for the preparation of a compound of the formula

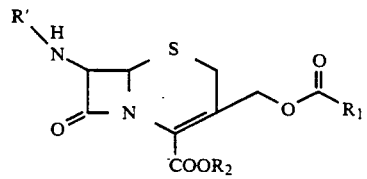

wherein

R₁ is the residue of an acid anhydride, said anhydride selected from the group consisting of acetic anhydride, butyric anhydride, heptanoic anhydride, pivalicanhydride, propionic anhydride, benzoic anhydride, phenylacetic anhydride, crotonic anhydride, chloroacetic anhydride, dichloroacetic anhydride or trifluoroacetic anhydride;

R₂ is hydrogen or a carboxy-protecting group; and

R' is an acyl group of the formula

where R is of the formula —(CH₂)tCOOH, wherein t is 1-3; which comprises reacting a compound of the formula

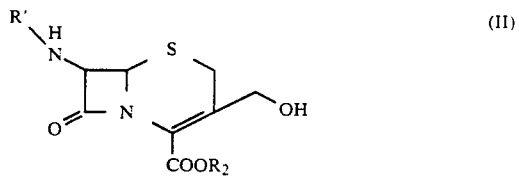

with an acid anhydride, as herein before described, in the presence of a base selected from the group of sodium hydroxide, potassium hydroxide or sodium phosphate, in an aqueous solution.

21. The process as recited in claim 20 wherein R₂ is hydrogen.

22. The process as recited in claim 20 wherein said anhydride is acetic anhydride.

23. The process as recited in claim 22 wherein said anhydride is present in the amount of about 10 to 20 molar equivalents to the compound of Formula II.

24. The process as recited in claim 20 wherein t is 3.

25. The process as recited in claim 20 wherein the reaction temperature is maintained at between about −10° C. to about 40° C.

26. The process as recited in claim 25 wherein said temperature is maintained at between about 0° C. to about 10° C.

27. The process as recited in claim 20 wherein the pH of the reaction is maintained between about 7 to about 11.

28. The process as recited in claim 27 wherein the pH is maintained between about 9 to about 10.5.

* * * * *